United States Patent

Saitoh et al.

(10) Patent No.: US 7,348,422 B2
(45) Date of Patent: Mar. 25, 2008

(54) FUSED PROTEIN, GENE THEREFOR, RECOMBINANT VECTOR, RECOMBINANT VIRUS, AND ITS USE

(75) Inventors: Shuji Saitoh, Kawasaki (JP); Yoshinari Tsuzaki, Kawasaki (JP); Noboru Yanagida, Kawasaki (JP)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 09/147,052

(22) PCT Filed: Mar. 28, 1997

(86) PCT No.: PCT/JP97/01084

§ 371 (c)(1),
(2), (4) Date: Apr. 5, 1999

(87) PCT Pub. No.: WO97/36924

PCT Pub. Date: Oct. 9, 1997

(65) Prior Publication Data

US 2001/0014335 A1 Aug. 16, 2001

(30) Foreign Application Priority Data

Mar. 29, 1996 (JP) ................................. 8-103548

(51) Int. Cl.
*C07H 21/04* (2006.01)
*A61K 39/00* (2006.01)
(52) U.S. Cl. .................. 536/23.4; 424/192.1; 530/350
(58) Field of Classification Search ............. 424/134.1, 424/184.1, 192.1, 201.1, 202.1, 204.1, 231.1, 424/232.1, 264.1, 190.1, 196.11, 197.11, 424/199.1, 229.1, 234.1, 278.1, 281.1, 282.1; 435/69.7, 69.8, 70.2, 340, 387.3; 530/388.4; 930/224
See application file for complete search history.

(56) References Cited

U.S. PATENT DOCUMENTS 5,286,639 A    2/1994    Yanagida et al. ......... 435/235.1

FOREIGN PATENT DOCUMENTS

| EP | 345021 | * 12/1989 |
| EP | 404576 | * 12/1990 |
| WO | WO 94/23019 | 10/1994 |

OTHER PUBLICATIONS

Blacklaws et al. 1990. Virology. vol. 177: 727-736, 1990.*
Calvert et al. 1993. J. of Virology. vol. 67(6): 3069-3076, 1993.*
Nazerian et al. 1992. J. of Virology. vol. 66 No. 3: 1409-1413, 1992.*
Yoshida et al. 1994. vol. 200: 484-493, 1994.*
Yoshida et al. 1994. vol. 204: 414-419, 1990.*
Yoshida et al.; Virology 200, pp. 484-493, 1994. See PCT Search Report.
Nazerian et al.; Journal of Virology, vol. 66, No. 3, pp. 1409-1413, Mar. 1992. See PCT Search Report.
DeLuca et al., Virology 122, pp. 411-423, 1982. See p. 4 of the specification.
Blacklaws et al., Virology 177, pp. 723-736, 1990. See p. 4 of the specification.

* cited by examiner

*Primary Examiner*—Robert A. Zeman
*Assistant Examiner*—Brian Gangle
(74) *Attorney, Agent, or Firm*—Kratz, Quintos & Hanson, LLP

(57) ABSTRACT

A DNA coding for a fusion protein comprising a polypeptide having the antigenicity of *Mycoplasma gallisepticum* and a polypeptide derived from Herpesvirus outer membrane protein, in which the polypeptide derived from the outer membrane protein has been ligated with the polypeptide having the antigenicity of *Mycoplasma gallisepticum* at the N terminus thereof, is prepared. The DNA is inserted into a region non-essential to growth of Avipox virus and the resulting recombinant Avipox virus is provided as a more potent recombinant virus as an anti-Mycoplasma vaccine.

6 Claims, 8 Drawing Sheets

//USO07348422B2

FUSED PROTEIN, GENE THEREFOR, RECOMBINANT VECTOR, RECOMBINANT VIRUS, AND ITS USE

TECHNICAL FIELD

The present invention relates to a novel fusion polypeptide of a polypeptide having the antigenicity of *Mycoplasma gallisepticum* and a polypeptide derived from the outer membrane protein of herpes viruses, a hybrid DNA coding for the fusion polypeptide, and a recombinant Avipox virus bearing the hybrid DNA, as well as a vaccine using the recombinant Avipox virus.

BACKGROUND ART

*Mycoplasma gallisepticum* (hereinafter sometimes abbreviated as MG) is a bacterium that causes reduction in an egg-laying rate and a hatching rate of eggs for poultry including chicken. This causative MG is widely spread all over the world so that a great deal of damage has been done to the poultry farming. For the prevention of MG, an inactivated vaccine or a live vaccine is currently utilized. However, the former live vaccine involves disadvantages of complicated inoculation procedures, short duration of immunity, expensive etc. The latter vaccine has such a defect that an unexpected disease might be developed by use in combination with live vaccine for other disease. Another disadvantage is that MG agglutination reaction system, which makes rapid detection of MG infection possible, can not be used for both inactivated and live vaccines.

It is expected that a protein derived from MG such as its antigenic protein for preventing from MG infection would be produced by genetic engineering technology and utilized as a vaccine.

The production system of the antigenic protein of *Mycoplasma gallisepticum* using *E. coli* or yeast by means of genetic engineering (JPA 2-111795, etc.) encounters such problems that depending upon a protein to be expressed, the antigenic protein is only expressed in a less amount, proteins of host origin might be by-produced and intermingled, host-derived pyrogen is removed only with difficulty, etc. For these reasons, studies are still focused on a recombinant virus to prepare antigenic proteins or on a recombinant live vaccine.

The expression of foreign genes using recombinant viruses, in most cases, genes of eucaryotes or viral genes are expressed. For this reason, addition or expression mode of sugar chains or the like is similar to the protein expression mechanism in infected cells. Thus, induction of an antibody titer to the expressed protein was relatively easy in vivo. However, genes of prokaryotes are rarely expressed in recombinant viruses. Because of different expression mode between eukaryotes and prokaryotes, it was difficult to say that a specific antibody was effectively induced (Austen et al., Protein Targeting and Selection, Oxford Univ. Press (1991)).

Turning to MG, recombinant viruses in which a gene coding for the protein has been incorporated are known by JPA 5-824646 and JPA 7-133295, WO 94/23019, etc. In particular, WO 94/23019 reveals that when a recombinant virus capable of expressing the antigenic protein of MG having a viral membrane anchoring region, which is obtained by ligating the signal membrane anchoring portion of HN gene of New Castle disease virus (hereinafter abbreviated as NDV) with the antigenic gene of MG, is inoculated as a recombinant live vaccine, the antibody is induced more effectively than a recombinant virus capable of expressing the antigenic gene of MG alone.

However, expression to such an extent is not always sufficient to achieve the desired effect as a vaccine.

Therefore, it is the urgent need to find an improved method for higher recognition of the antigen in order to develop an effective vaccine against MG infections.

Outer membrane proteins other than NDV mentioned above are known also in the genus Herpesvirus, etc. With respect to glycoproteins B(gB), C(gC), D(gD), H(gH) and I(gI) of herpes simplex viruses; proteins gBh, gCh, gDh, gHh and gIh of Marek's disease viruses (hereinafter often referred to as MDV) corresponding to herpes simplex virus glycoproteins gB, gC, gD, gH and gI and proteins of the genus Herpesvirus homologous to those proteins described above, etc., the nucleotide sequence and amino acid sequence of these proteins are known. It is also known that a part of these proteins induces neutralizing antibodies of herpes simplex viruses (Deluca et al., Virology, 122, 411-423 (1982)). It is further known that neutralizing antibodies can be induced by incorporating genes coding for these proteins into vaccinia viruses and expressing the genes (Blacklaws et al., Virology, 177, 727-736 (1990)).

However, investigations to make use of signal sequences of such outer membrane proteins of the genus Herpesvirus were hardly made so far.

DISCLOSURE OF THE INVENTION

Under the situation of the prior art stated above, the present inventors have made extensive studies to provide a recombinant virus capable of expressing a Mycoplasma antigenic protein having an enhanced infection prevention activity in large quantities, which allows a host to recognize the antigen highly efficiently. As a result, it has been found that by infecting to a host a recombinant Avipox virus, in which a hybrid DNA obtained by ligating a DNA of the outer membrane protein of the genus Herpesvirus with a DNA of the antigenic protein of *Mycoplasma* has been inserted, the antigen recognizing ability of the host can be markedly improved. The present invention has thus been accomplished.

Accordingly, the present invention provides:

a fusion protein comprising a polypeptide having the antigenicity of *Mycoplasma gallisepticum* (hereinafter sometimes referred to as *Mycoplasma*-derived polypeptide) and a polypeptide derived from the outer membrane protein of a herpes virus (hereinafter sometimes referred to as Herpesvirus-derived polypeptide) characterized in that the polypeptide derived from outer membrane protein is ligated with the polypeptide having the antigenicity of *Mycoplasma gallisepticum* at the N terminus thereof;

a hybrid DNA coding for the fusion protein;

a recombinant Avipox virus in which the hybrid DNA has been incorporated; and, a live vaccine comprising the recombinant Avipox virus as an effective ingredient.

BEST MODE FOR PRACTICING THE INVENTION

Mycoplasma-derived Polypeptides and Genes Therefor

Figure 1:
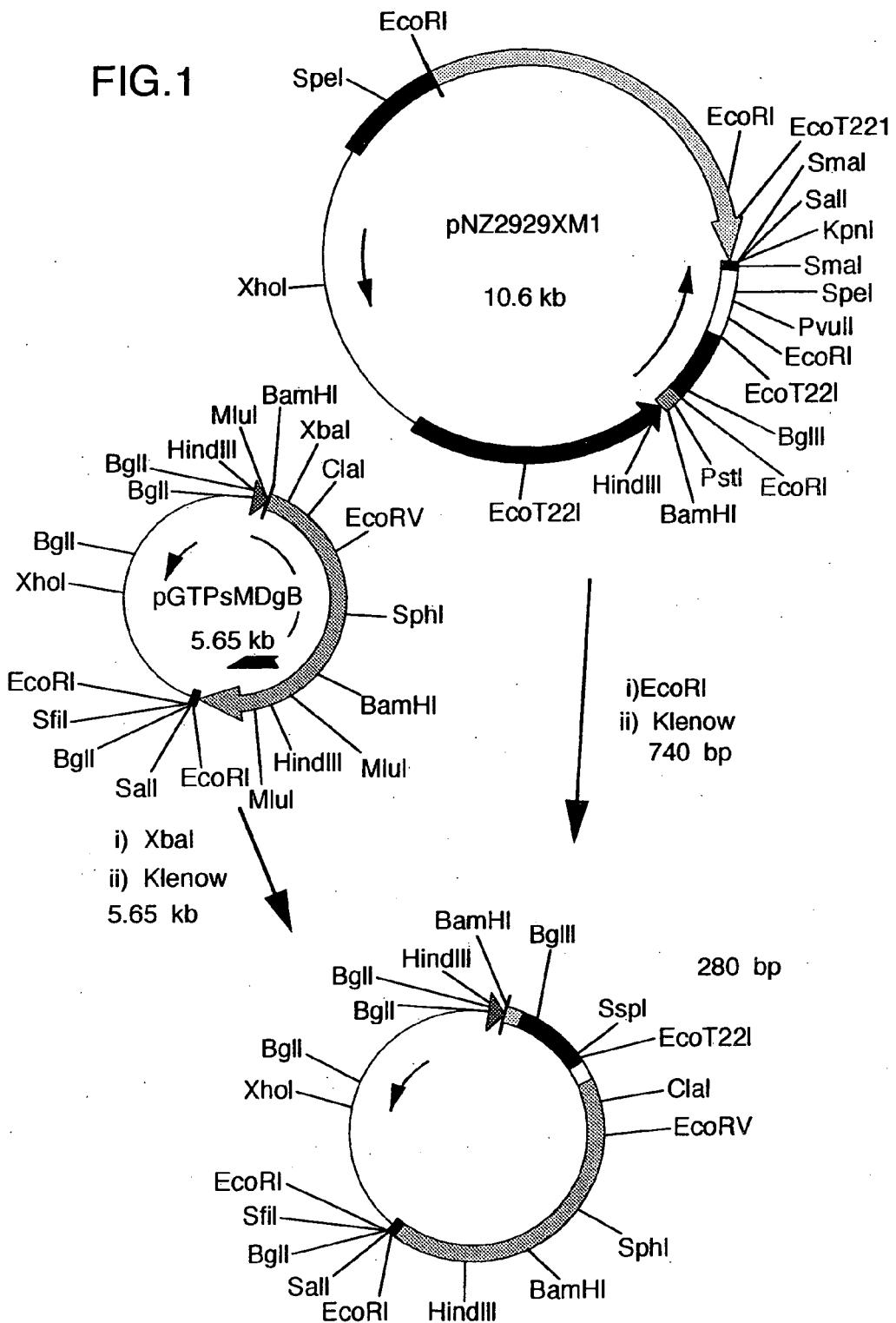
FIG. 1 is a drawing for explaining procedures for construction of pNZ40K-S.
Figure 2:
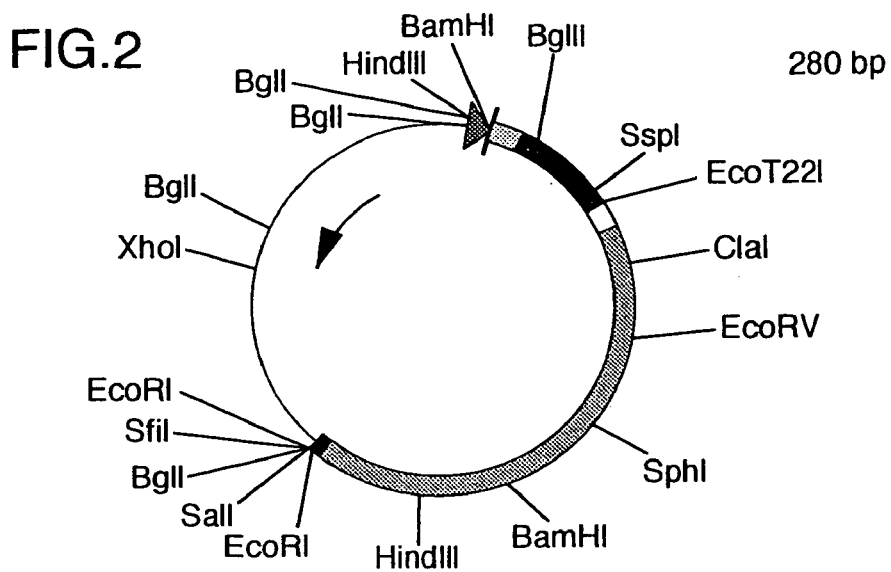
FIG. 2 is a drawing for explaining procedures for construction of pNZ40K-S.
Figure 2:
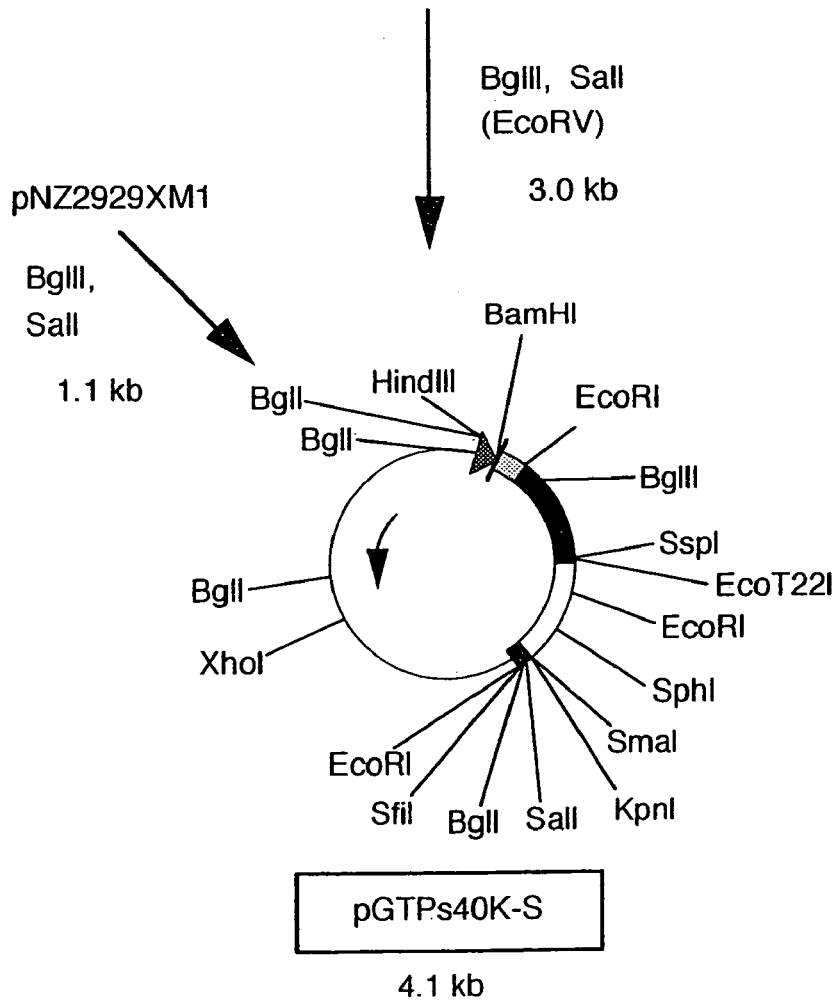
Figure 3:
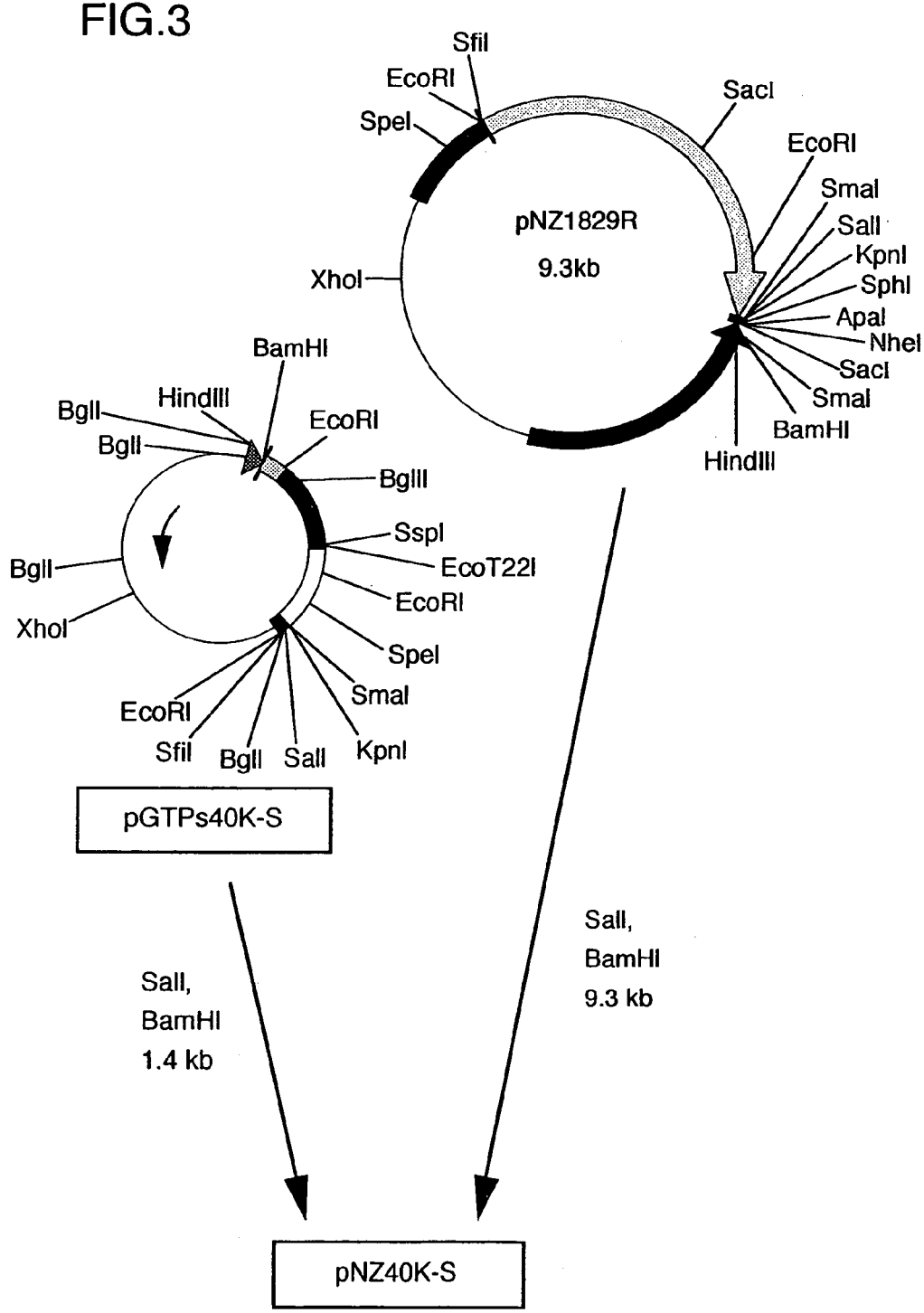
FIG. 3 is a drawing for explaining procedures for construction of pNZ40K-S.

In the present invention, the term Mycoplasma-derived polypeptides is used to mean the antigenic proteins that cause an antigen-antibody reaction with MG immune serum or MG infected serum and that are derived from MG. These polypeptides are not restricted to proteins per se that native *Mycoplasma gallisepticum* expresses, and may include modified polypeptides. For example, one or more amino acids of the polypeptides may be modified naturally or artificially in a conventional manner such as site-specific mutation, etc. (JPB 6-16709, etc.) through loss, addition, insertion, deletion, substitution, etc. Of course, the proteins, even after such modification, should contain the epitope showing the antigenicity. For determination of the epitope region, there are available known methods based on the peptide scanning technique such as the method of Geysen et al. (J. Immunol. Meth., 102, 259-274 (1987)), the method of Hopp et al., (Proc. Natl. Acad. USA, 78, 3824-3828 (1981)), the method Chou et al. (Advances in Enzymology, 47, 145-148 (1987)), etc.

Specific examples of the peptides having the antigenicity include antigenic proteins disclosed in JPA 2-111795 (U.S. patent application Ser. Nos. 359,779, 07/888,320 and 08/299,662), JPA 5-824646 (U.S. Pat. No. 5,489,430), WO 94/23019 (U.S. patent application Ser. No. 08/525,742, JPA 6-521927) and proteins of *Mycoplasma gallisepticum* containing the amino acid sequences of those proteins. Of course, so long as the epitope is contained therein, a part of the peptides described above may also be usable.

Of these peptides, preferred are the polypeptide of about 40 killodaltons (kd) described in JPA 5-824646, the polypeptide of about 66 kd encoded by TM-66 gene and the polypeptide of about 67 kd encoded by TM-67 gene described in JPA 5-521927, which are designated as SEQ NO: 16 and SEQ NO: 27 therein.

In the present invention, genes of the *Mycoplasma*-derived polypeptides bear DNA sequences coding for the polypeptide having the antigenicity of *Mycoplasma gallisepticum* described above. Such DNA can be obtained by synthesis or acquired from wild bacteria belonging to *Mycoplasma gallisepticum*. Specific examples of such bacteria are strains R, S6, KP-13, PG31, etc. DNA may also be derived from MG isolated from wild strains. These genes can also be modified by loss, addition, insertion, deletion, substitution, etc. in a conventional manner as described in Methods in Enzymology, etc.

Herpesvirus-derived Polypeptides and Genes Thereof

The Herpesvirus-derived polypeptides in the present invention refer to polypeptides derived from proteins that construct an envelope of viruses belonging to the genus Herpesvirus. The Herpesvirus-derived polypeptides may not always be the full length of the proteins. Where the polypeptides are used solely to be expressed on the surface of cell membranes function as fusion proteins, it is sufficient for the polypeptide to contain a membrane anchor and a signal sequence therein, and where the polypeptides are employed for secretion, the polypeptides may contain only a signal sequence for that purpose. The outer membrane proteins may be either type I or type II of the outer membrane proteins. The signal sequence and the membrane anchoring sequence are both readily detectable by analyzing the amino acid sequence in the hydrophobic peptide region at the carboxyl terminus or amino terminus thereof.

Specific examples of the outer membrane protein include gB, gC, gD, gH and gI which are glycoproteins of herpes simplex viruses, and gBh, gCh, gDh, gHh and gIh of MDV corresponding to herpes simplex viruses glycoproteins gB, gC, gD, gH and gI, and proteins of the genus Herpesvirus homologous to the proteins described above.

Of course, polypeptides bearing the epitope other than the signal sequence of the outer membrane proteins may also be ligated with the aforesaid polypeptides having the antigenicity. By the ligation it is expected that the epitope will give the immunity to the living body in vivo.

In the present invention, the genes for the *Mycoplasma*-derived polypeptides contain DNA sequences coding for the Herpesvirus-derived polypeptides described above and such DNAs can be synthesized or acquired from naturally occurring herpes viruses. These genes may also be modified by loss, addition, insertion, deletion, substitution, etc. in a conventional manner as described in Methods in Enzymology, etc.

Fusion Protein and Hybrid DNA

The fusion proteins of the present invention are obtained by incubating a recombinant Avipox virus inserted hydrid DNA, which will be later described, in culture cells such as chick embryo fibroblast cells (hereinafter referred to as CEF cells) or embryonated chorioallantoic membrane cells, etc.

The thus obtained fusion proteins can be employed as a component vaccine.

The hybrid DNA of the present invention comprises the gene for the *Mycoplasma*-derived polypeptide and the gene for the Herpesvirus-derived polypeptide, which are ligated with each other directly or via an optional DNA sequence.

The hybrid DNA of the present invention can be produced in a conventional manner, for example, by a method in which the outer membrane protein and the antigenic protein of *Mycoplasma gallisepticum* are digested with restriction enzymes, respectively, and the resulting ligatable DNA fragment coding for the outer membrane protein of herpes viruses or for the signal sequence of the outer membrane protein is ligated with the resulting ligatable DNA fragment coding for the antigenic protein of *Mycoplasma gallisepticum*, using a ligase directly or via an appropriate linker.

Specific examples of the amino acid sequences for the fusion proteins of the present invention include SEQ ID NO: 2 and SEQ ID NO: 4. The sequence of the antigenic protein of 40 killodaltons derived from *Mycoplasma gallisepticum* is found in amino acids 64-456 of SEQ ID NO: 2 and in amino acids 693-1086 of SEQ ID NO: 4. The signal sequence of outer membrane protein gB derived from MDV is found in amino acids 1-63 of SEQ ID NO: 2. In SEQ ID NO: 4, amino acids 1-672 correspond to almost the full length of outer membrane protein gB derived from MDV. Specific examples of nucleotide sequences of the hybrid DNAs coding for these fusion proteins are those shown by SEQ ID NO: 1 and SEQ ID NO: 3.

These fusion proteins and hybrid DNAs are given by way of examples but are not deemed to be limited thereto.

Recombinant Avipox Virus

The recombinant Avipox virus of the present invention is a recombinant Avipox virus in which the aforesaid DNA or hybrid DNA has been inserted in the non-essential region. The recombinant Avipox virus of the present invention can be constructed in a conventional manner, e.g., by the method described in Japanese Patent Application Laid-Open No. 1-168279. That is, the non-essential region of Avipox virus is incorporated into a DNA fragment to construct a first recombinant vector.

As the non-essential region of Avipox virus which is used in the present invention, there are a TK gene region of quail pox virus, a TK region of turkey pox virus and DNA fragments described in JPA 1-168279, preferably a region which causes homologous recombination with EcoRI fragment of about 7.3 Kb, HindIII fragment of about 5.2 Kb, EcoRI-HindIII fragment of about 5.0 Kb, BamHI fragment of about 4.0 Kb, described in the patent specification supra.

Examples of the vector used in the present invention include plasmids such as pBR322, pBR325, pBR327, pBR328, pUC7, pUC8, pUC9, pUC18, pUC19, and the like; phages such as λ phage, M13 phage, etc.; cosmid such as pHC79 and the like.

The Avipox virus used in the present invention is not particularly limited so long as it is a virus infected to avian. Specific examples of such a virus include pigeon pox virus, fowl pox virus (hereafter abbreviated as FPV), canary pox virus, turkey pox virus, preferably pigeon pox virus, FPV and turkey pox virus, more preferably pigeon pox virus and FPV. Specific examples of the most preferred Avipox virus include FPVs such as ATCC VR-251, ATCC VR-249, ATCC VR-250, ATCC VR-229, ATCC VR-288, Nishigahara strain, Shisui strain, CEVA strain and a viral strain among CEVA strain-derived viruses which forms a large plaque when infected to chick embryo fibroblast, and a virus such as NP strain (chick embryo-attenuated pigeon pox virus Nakano strain), etc. which is akin to FPV and used as a fowlpox live vaccine strain. These strains are commercially available and readily accessible.

Next, the hybrid DNA of the present invention is inserted into the non-essential region of the first recombinant vector described above to construct a second recombinant vector. In general, the hybrid DNA employed may have any nucleotide sequence, irrespective of synthetic or natural one, so long as the hybrid DNA effectively functions as a promoter in the system of transcription possessed by Avipox viruses. Accordingly, not only promoters inherent to Avipox viruses such as promoters for Avipox virus-derived genes coding for thymidine kinase but also DNAs derived from viruses other than Avipox viruses and DNAs derived from eukaryotes or prokaryotes may also be employed in the present invention, insofar as these substances meet the requirements described above. Specific examples of such promoters include promoters for vaccinia viruses (hereinafter often referred to as VV) as described in Journal of Virology, 51, 662-669 (1984), more specifically, a promoter of VV gene coding for 7.5 K polypeptide, a promoter of VV gene coding for 19 K polypeptide, a promoter of VV gene coding for 42 K polypeptide, a promoter of VV gene coding for thymidine kinase, a promoter of VV gene coding for 28 K polypeptide, etc. Furthermore, there may be used a synthetic promoter obtained by modification of the Moss et al. method (J. Mol. Biol., 210, 49-76 and 771-784, 1989), Davidson's synthetic promoter, a promoter obtained by modifying a part of the Davidson's promoter through deletion or change in such a range that the promoter activity is not lost (e.g., TTTTTTTTTTTG-GCATATAAATAATAATAAATACAATAAT-TAATTACGCGTAAAAA TTGAAAAACTATTCTAATT-TATTGCACTC SEQ ID NO: 5, TTTTTTTTTTTTTTTTTTTTG-GCATATAAATAATAAATACAATAATTAATTACGCGT AAAAATTGAAAAACTATTCTAATTTATTGCACTC SEQ ID NO. 6 etc.).

Further in view of easy detection of the recombinant virus, a marker gene such as a DNA coding for β-galactosidase may also be inserted.

The recombinant Avipox virus can be constructed by transfecting the second recombinant vector described above to animal culture cells, which has been previously infected with Avipox virus, and causing homologous recombination between the vector DNA and the viral genome DNA. The animal culture cells used herein can be any cells, so long as Avipox can grow in the cells. Specific examples of such animal culture cells are CEF cells, embryonated egg chorioallantoic membrane cells, and the like.

The objective recombinant Avipox virus is isolated from the virus infected to host cells by plaque hybridization, etc.

Live Vaccine

The recombinant virus of the present invention constructed by the method described above can be inoculated to avian as a live vaccine for *Mycoplasma gallisepticum* infection.

The live vaccine of the present invention is prepared by, e.g., the following method, though the process is not particularly limited thereto. The recombinant virus of the present invention is infected to cells in which the virus can grow (hereafter referred to as host cells). After the recombinant virus grows, the cells are recovered and homogenated. The homogenate is centrifuged to separate into the precipitates and the high titer supernatant containing the recombinant virus. The resulting supernatant is substantially free of host cells but contains the cell culture medium and the recombinant virus and hence can be used as a live vaccine. The supernatant may be diluted by adding a pharmacologically inert carrier, e.g., physiological saline, etc. The supernatant may be freeze-dried to be provided for use as a live vaccine. A method for administration of the live vaccine of the present invention to fowl is not particularly limited and examples of the administration include a method for scratching the skin and inoculating the live vaccine on the scratch, effecting the inoculation through injection, oral administration by mixing the live vaccine with feed or drinking water, inhalation by aerosol or spray, etc. In order to use as the live vaccine, the dosage may be the same as ordinary live vaccine; for example, approximately $10^2$ to $10^8$ plaque forming unit (hereinafter abbreviated as PFU) is inoculated per chick. Where the inoculation is effected by injection, the recombinant virus of the present invention is generally suspended in about 0.1 ml of an isotonic solvent such as physiological saline and the resulting suspension is provided for use. The live vaccine of the present invention can be lyophilized under ordinary conditions and can be stored at room temperature. It is also possible to freeze the virus suspension at −20 to −70° C. and store the frozen suspension.

Particularly where the genes coding for the polypeptides derived from the outer membrane proteins of herpes viruses described above are those coding for polypeptides having more than one epitope of herpes viruses, preferably having at least 90% homology to native outer membrane proteins, the live vaccine of the present invention functions as a vaccine for both *Mycoplasma gallisepticum* infection and Avipox viral infection. In addition, the live vaccine of the present invention can also function as an effective vaccine for infection with herpes virus originating from outer membrane proteins. That is, the live vaccine of the present invention can be used as a so-called trivalent vaccine.

EXAMPLES

Example 1

Construction of Recombinant pNZ40K-S Bearing Hybrid DNA Ligating TTM-1 Protein DNA Immediately After the Signal of gB Gene for Marek's Disease Virus (cf. FIGS. 1. 2 and 3)

First, plasmid pUCgB bearing gB gene of Marek's disease virus, disclosed in JPA 6-78764, was digested with restriction enzymes BamHI and SalI to recover a fragment of 3.9 kb.

Separately, plasmid pGTPs was constructed by digesting plasmid pNZ1729R (Yanagida et al., J. Virol., 66, 1402-1408 (1992)) with HindIII and SalI, inserting the resulting DNA fragment of about 140 bp into pUC18 at the HindIII-SalI site thereof, further inserting synthetic DNA (5'-AGCT-GCCCCCCCGGCAAGCTTGCA-3') SEQ ID NO: 7 at the HindIII-PstI site, then inserting synthetic DNA (5'-TCGA-CATTTTTATGTGTAC-3') SEQ ID NO: 8 at the SalI-EcoRI site and finally inserting synthetic DNA (5'-AATCGGC-CGGGGGGGCCAGCT-3') SEQ ID NO: 9 at the SacI-EcoRI site.

The thus obtained pGTPs was digested with restriction enzymes SalI and BamHI and then ligated with the aforesaid 3.9 kb fragment using a ligase to obtain pGTPsMDgB. Thereafter, pNZ2929XM1 disclosed in WO 94/23019 was digested with EcoRI to recover a fragment of 740 bp and then obtained a blunt end with T4 DNA polymerase. On the other hand, pGTPsMDgB was also digested with XbaI and then obtained a blunt end with T4 DNA polymerase. Subsequently, pGTPsMDgB was ligated with the 740 bp fragment having the blunt end using a ligase to construct a new plasmid. This new plasmid was digested with BglII and SalI to recover a fragment of 3.0 kb. The 3.0 kb fragment was ligated with the 1.1 kb fragment obtained through digestion of pNZ2927XM1 with BglII and SalI, using a ligase. Thus, there was obtained a plasmid ligating the N terminus of TTM-1 gene at the C terminus of the signal sequence of gB gene of Marek's disease virus.

Finally, a fragment of 1.4 kb obtained by digestion of pGTPs40K-S with SalI and BamHI was ligated with a fragment of 9.3 kb obtained by digestion of plasmid pNZ1829R with SalII and BamHI, using a ligase. The objective plasmid pNZ40K-S of 10.7 kb was thus constructed for use in recombination.

Example 2

Figure 4:
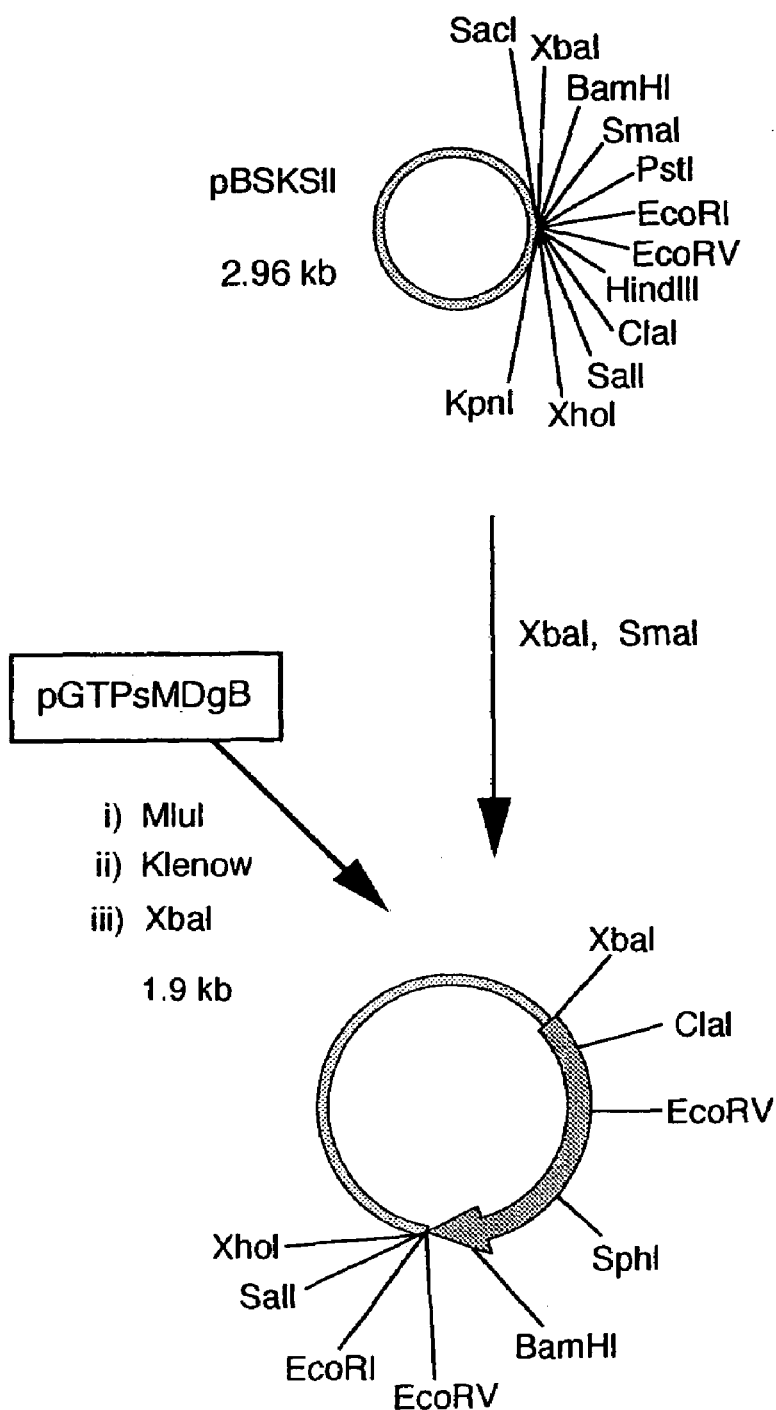
FIG. 4 is a drawing for explaining procedures for construction of pNZ40K-C.
Figure 5:
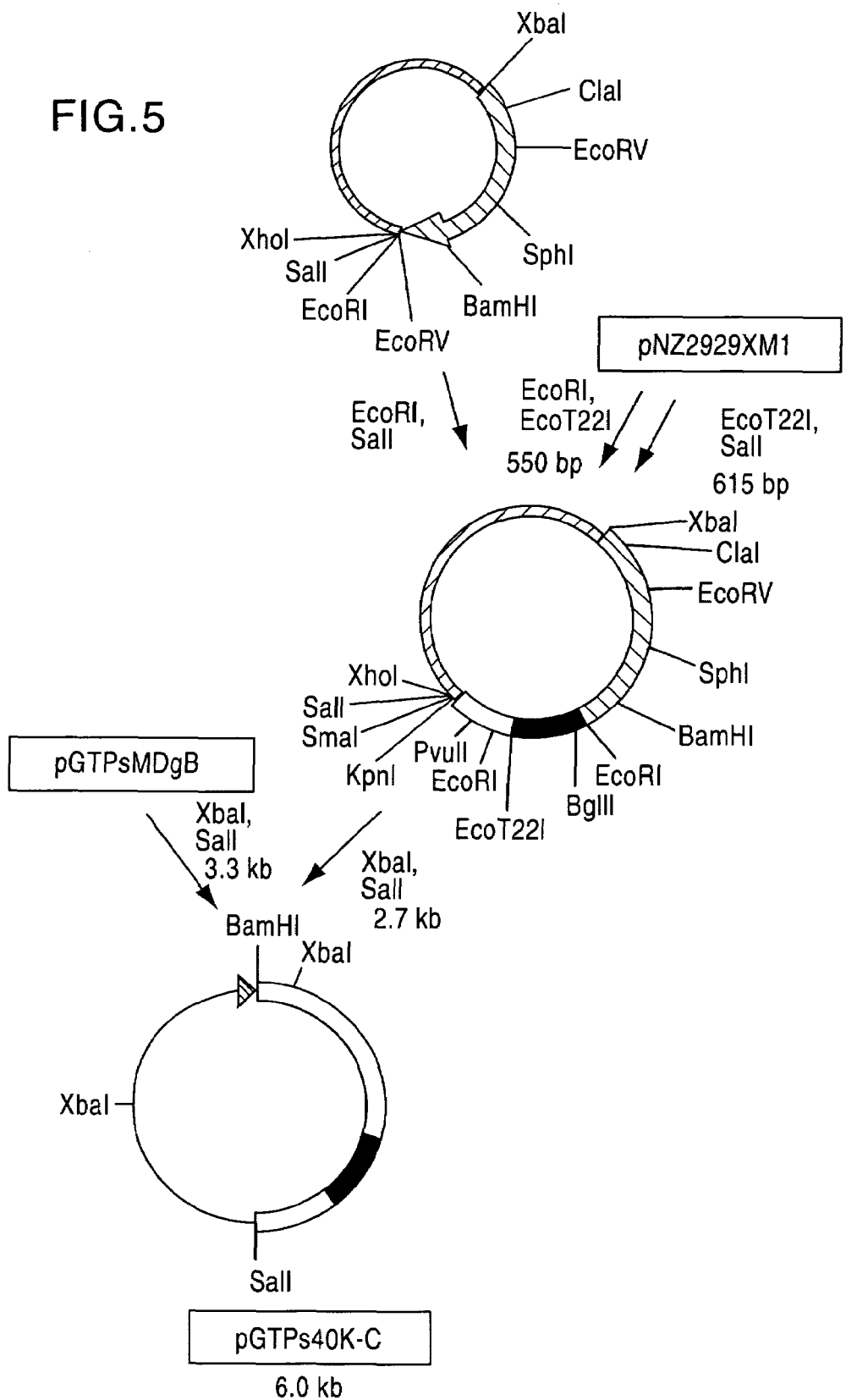
FIG. 5 is a drawing for explaining procedures for construction of pNZ40K-C.
Figure 6:
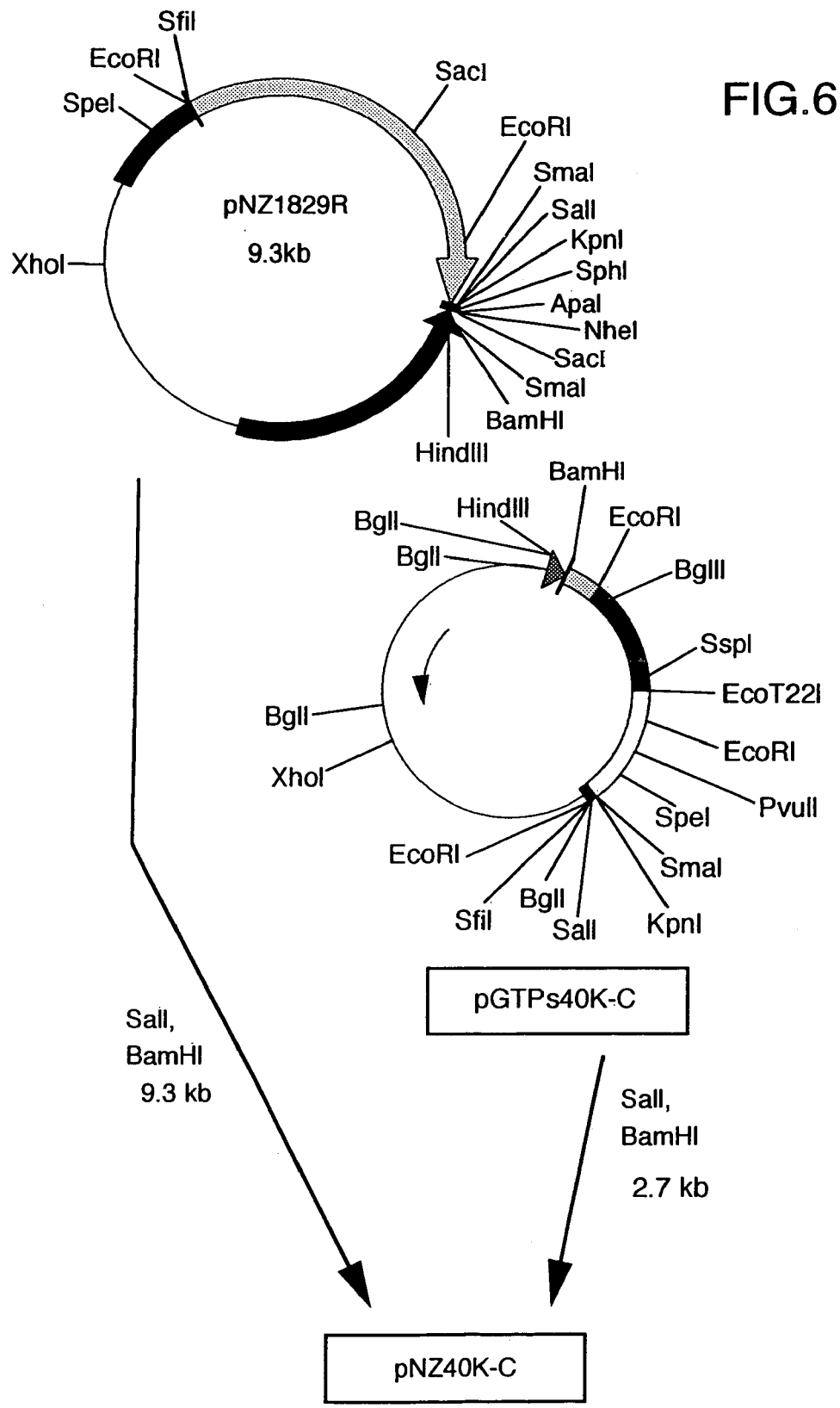
FIG. 6 is a drawing for explaining procedures for construction of pNZ40K-C.

Construction of Recombinant pNZ40K-C Bearing Hybrid DNA Ligating TTM-1 Protein DNA at the C Terminus of gB Gene for Marek's Disease Virus (cf. FIGS. 4. 5 and 6)

After plasmid pGTPsMDgB obtained in Example 1 was digested with restriction enzyme MluI, and then obtained a blunt end with T4 DNA polymerase, which was followed by digestion with restriction enzyme XbaI to recover a fragment of 1.9 kb. Separately, pBluescript II (made by Toyobo Co., Ltd., hereinafter abbreviated as pBSKSII) was digested with restriction enzymes XbaI and SmaI. The resulting fragment was ligated with the 1.9 kb fragment obtained above using a ligase to give a plasmid. The resulting plasmid was digested with restriction enzymes EcoRI and SalI. The resulting fragment was ligated with the 550 bp fragment and the 615 bp fragment, both obtained by digestion of pNZ2929XM1 with restriction enzymes EcoRI and Eco T22I and with restriction enzymes EcoT22I and SalI, respectively, using a ligase to construct a plasmid. The thus obtained plasmid was digested with restriction enzymes XbaI and SalI. The resulting 2.7 kb fragment was ligated with the 3.3 kb fragment obtained by digestion of pGTPsMDgB with restriction enzymes XbaI and SalI, using a ligase. Plasmid pGTPs40K-C ligating the TTM-1 gene at the N terminus thereof with the gB gene for Marek's disease virus at the C terminus thereof was thus obtained.

Finally, a fragment of 2.7 kb obtained by digestion of pGTPs40K-C with SalI and BamHI was ligated with a fragment of 9.5 kb obtained by digestion of plasmid pNZ1829R with SalI and BamHI, using a ligase. The objective plasmid pNZ40K-C of 12.2 kb for recombination was thus constructed.

Example 3

Construction of Recombinants FPV 40K-C and 40K-S and Purification Thereof

NP strain, which is a fowlpox live vaccine strain, was infected to monolayered CEF at m.o.i.=0.1. Three hours after, these cells were scraped off from the monolayer by a treatment with trypsin to form a cell suspension. After $2\times10^7$ cells in the suspension were mixed with 10 µg of plasmid pNZ40K-C or pNZ40K-S for use in recombination, the mixture was suspended in Saline G (0.14 M sodium chloride, 0.5 mM potassium chloride, 1.1 mM disodium hydrogenphosphate, 1.5 mM potassium dihydrogenphosphate, 0.5 mM magnesium chloride hexahydrate, 0.011% glucose). The suspension was subjected to electrophoresis under conditions of 3.0 kV cm$^{-1}$, 0.4 msec and 25° C., using GENE PULSER (trademark) (manufactured by Bio-Rad Co., Ltd.) at room temperature. The plasmid-infected cells were then cultured at 37° C. for 72 hours. The cells were lysed by freezing and thawing 3 times to recover viruses containing the recombinant virus.

The recovered recombinant virus was selected as follows. The recovered viral solution was infected to monolayered CEF and 10 ml of agar solution containing growth medium was overlaid thereon. After agar was warmed at room temperature, incubation was performed at 37° C. until plaques of FPV appeared. Then agar medium containing Bluo-gal in a concentration of 200 µg/ml was overlaid on the agar followed by incubation at 37° C. for further 48 hours. Among all of the plaques, about 1% of the plaques were colored blue. These blue plaques were isolated and recovered. By the same procedures, isolation and recovery were repeated to purify the virus until all the plaques were stained to blue. In general, the repeated procedures were terminated by 3 to 4 days. The purified strains were named 40K-C and 40K-S, respectively. In 40K-C and 40K-S, each position of the DNAs inserted was confirmed by dot blotting hybridization and Southern blotting hybridization.

Example 4

Expression of TTM-1 Polypeptide in Cells Infected with 40K-C and 40K-S

In order to confirm that 40K-C and 40K-S could express TTM-1 polypeptide in infected cells, Western blotting was performed using anti-*Mycoplasma gallisepticum* S6 strain sera. Virus 40K-C or 40K-S was infected to CEF and cultured at 37° C. until plaques were formed. The cells were then scraped off with a cell scraper and centrifuged at 8000 G for 20 minutes together with the culture supernatant. The cell-containing precipitates (hereinafter referred to as pellets) were recovered. After washing with PBS, the pellets were centrifuged at 8000 G for 20 minutes followed by rinsing to recover the pellets. The pellets were then suspended in 150 μl of PBS. From the suspension 50 μl was taken and added with the same volume of Laemmli's buffer (containing 10% mercapto-ethanol). After boiling for 3 minutes, the mixture was subjected to sodium dodecyl sulfate-polyacrylamide gel electrophoresis (hereinafter abbreviated as SDS-PAGE) in accordance with the Laemmli's method (Nature, 227, 668-685 (1970)). The polypeptides isolated on the SDS-PAGE-completed gel were transferred onto a polyvinylidene difluoride membrane (IMMOBILON (trademark) Transfer Membrane, made by Millipore Inc., hereinafter simply referred to as membrane) according to the method of Burnett et al., (A. Anal. Biochem., 112, 195-203 (1970)) or by the method of Towbin et al. (Proc. Natl. Acad. Sci., 75, 4350-4354 (1979)) by means of electrophoresis. The membrane was dipped for an hour into PBS containing 3% skimmed milk for blocking not to cause any non-specific binding. Next, the membrane was dipped for an hour in PBS in which chick anti-*Mycoplasma gallisepticum* S6 strain serum was diluted to 1000-fold.

Subsequently, the membrane was rinsed with PBS and then dipped for an hour in PBS containing alkaline phosphatase conjugate anti-chick IgG as a secondary antibody. After the membrane was rinsed with PBS, a color-forming reaction was carried out in 10 ml of a solution containing 100 mM Tris hydrochloride (pH 7.5), 0.15 M sodium chloride and 50 mM magnesium chloride, using Nitro Blue Tetrazolium salt (NBT, made by GIBCO-BRL Inc.) and 5-bromo-4-chloro-3-indole phosphate-p-toluidine (BCIP, made by GIBCO-BRL Inc.) as color-forming substrates.

Figure 7:
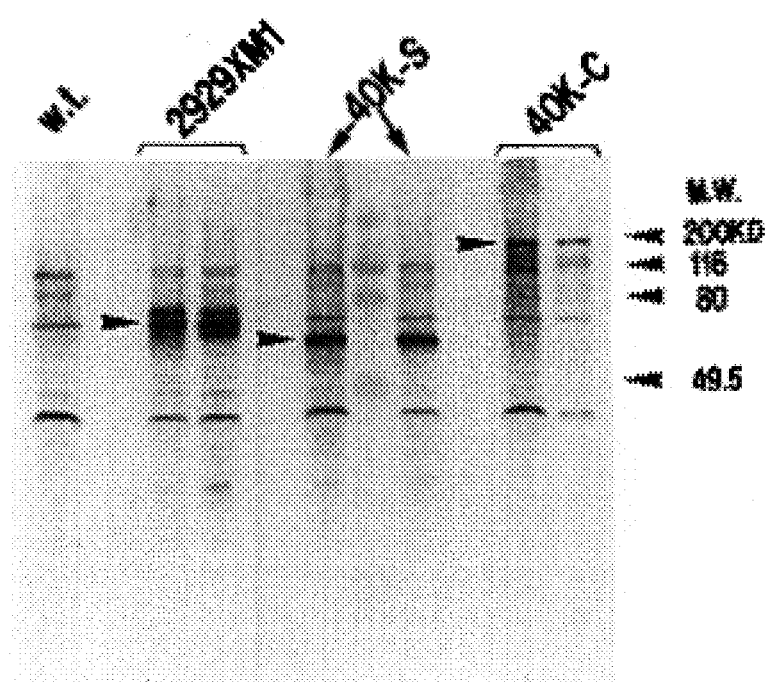
FIG. 7 shows the results of Western blotting by which expression of TTM-1 polypeptide was confirmed.

The results of the Western blotting are shown in FIG. 7.

As shown in FIG. 7, proteins could be confirmed with the cells infected both with 40K-S and 40K-C as those reactive at the objective positions. It was thus verified that the expected proteins could be expressed in the recombinant FPV infected cells.

Example 5

Antibody-inducing Capability of Recombinant FPV-inoculated Chicken

After 40K-C and 40K-S were cultured in CEF at 37° C. for 48 hours, the procedure of freezing and thawing was repeated twice to recover the cell suspension. The cell suspension was adjusted to have a virus titer of $10^6$ pfu/ml and then inoculated to SPF chicken (Line M, Nippon Seibutsu Kagaku Kenkyusho) of 7 days old at the right wing web in a dose of 10 μl through a stab needle. After the inoculation, take of the pock was observed and the sera were collected 2 weeks after the inoculation. The antibody titer of the sera collected was determined by ELISA (Enzyme Linked Immuno Sorbent Assay). The purified TTM-1 polypeptide was dissolved in a bicarbonate buffer solution in a concentration of 1 μg/well. After adsorption to a 96 well microtiter plate, blocking was effected with skimmed milk to prevent the subsequent non-specific adsorption. Next, a dilution of the sample serum was charged in each well and then horse radish peroxide-labeled anti-chicken immunoglobulin antibody (rabbit antibody) was added thereto as a secondary antibody. After thoroughly washing, 2,2'-azino-diethylbenzothiazoline sulfonate was added to the mixture as a substrate and a relative dilution magnification of the antibody was measured with an immuno-reader in terms of absorbance at a wavelength of 405 nm. As a primary antibody for control, anti-TTM-1 polypeptide chicken serum was used. The results are shown in Table 1.

TABLE 1

Antibody titer of rFPV-inoculated chicken by ELISA

| Methods for treating chicken | Antibody titer of anti-TTM-1 polypeptide |
|---|---|
| 40K-S inoculation | 1024 |
| 40K-C inoculation | 512 |
| TTM-1 immunization | 512 |
| non-inoculated | 1 |

Antibody titer: Dilution magnification when the antibody titer of the group of non-inoculated chicken serum dilution was made 1

As shown in Table 1, the results reveal that when 40K-C or 40K-S was inoculated to chicken, the anti-TTM-1 antibody titer in sera was increased to the level higher than the antibody titer in sera from the chicken immunized with TTM-1 polypeptide. From the results it was confirmed that the recombinant FPV could significantly induce the antibody titer to the inoculated chicken.

Example 6

Mycoplasma Challenge Test Against Recombinant FPV-inoculated Chicken

The challenge test was conducted basically in accordance with the standard for biological preparations for animals. The method is briefly described below.

Strains 40K-C and 40K-S were inoculated to SPF chicken (Line M, Japan Biological Science Laboratory) of 5 weeks old at the right wing web in a dose of 10 μl through a stab needle. After the inoculation, take of the pock was observed to verify completion of the immunization. Two weeks after the inoculation, *Mycoplasma gallisepticum* strain R was forced to be intratracheally administered in a dose of $10^4$ to $10^5$ cfu/chick, whereby infection was made sure. On Day 14 after the infection, the chicken were enthanized with NEMBTAL (trademark)(manufactured by Abbot). Tissue sections were prepared from the tracheal lesion and scores of the tracheal lesion were determined based on the thickness of tracheal mucous membrane and histological findings. The scores were also determined by the above standard for biological preparations. An average of scores for the tracheal lesion observed with each chick in the groups was made the score for the respective groups. For information, criteria to determine tracheal lesion scores is shown in Table 2.

TABLE 2

Standard Criteria for Scoring Tracheal Lesion

| Thickness of Mucous Membrane | Histological Finding | Score |
|---|---|---|
| 90 μm~ | normal appearance of ciliated epitherial cells and mucus gland | 0 |
| | In the lamina propria, slight infiltration of round cells or | 1 |

TABLE 2-continued

Standard Criteria for Scoring Tracheal Lesion

| Thickness of Mucous Membrane | Histological Finding | Score |
|---|---|---|
| 90 μm~110 μm | minute nest can be found, but epithelial cell-layer is normal. | |
| | Epitherial cell are degenarated or diseminated, and the lamina propria is moderately thickened due to round cells infiltration. | 2 |
| 110 μm~ | Squamous metaplasia of surface epithelium and lamina propria is extremely thickened due to capillary hyperplasia and rounded cells infiltration; cell debris are accumulated in the tracheal lumen. | 3 |

Figure 8:
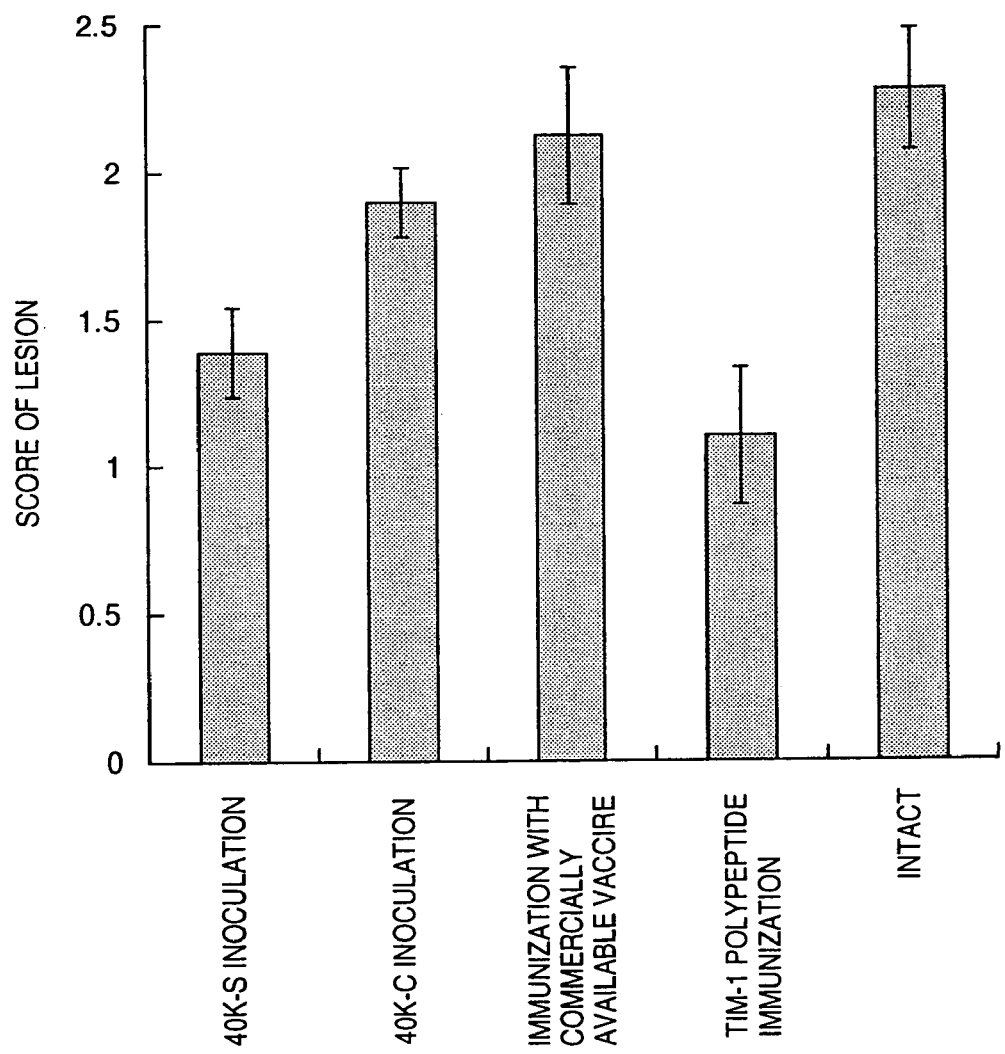
FIG. 8 shows scores of the tracheal lesion caused.

The results of evaluation are shown in Table 3 and FIG. 8.

TABLE 3

Means tracheal lesion scores in FPV-inoculated Chicken

| | Lesion Score | |
|---|---|---|
| Vaccination | Average | Standard Error |
| 40K-S | 1.38 | 0.16 |
| 40K-C | 1.89 | 0.13 |
| Commercial vaccine | 2.11 | 0.24 |

TABLE 3-continued

Means tracheal lesion scores in FPV-inoculated Chicken

| | Lesion Score | |
|---|---|---|
| Vaccination | Average | Standard Error |
| TTM-1 polypeptide | 1.09 | 0.23 |
| None | 2.27 | 0.21 |

As is clearly noted from the results above, the lesion scores of chicken inoculated with 40K-C and 40K-S are obviously low as compared to that of the non-inoculated chicken, indicating that the vaccines of the present invention clearly imparted to chicken the effective infection prevention for *Mycoplasma* challenge. Thus, the results reveal that 40K-C and 40K-S could be effective vaccines for *Mycoplasma gallisepticum*.

INDUSTRIAL APPLICABILITY

According to the present invention, the fusion proteins of the polypeptides derived from antigenic proteins of *Mycoplasma gallisepticum* and the polypeptides derived from outer membrane proteins of herpes viruses are obtained. The fusion proteins are effective as vaccines for anti-*Mycoplasma* infection, anti-chicken pox or anti-Marek's disease. By use of the hybrid DNAs coding for the fusion proteins, *Mycoplasma gallisepticum* antigenic proteins can be efficiently provided on the surface of host cells. Moreover, the hybrid DNAs can secrete the antigenic proteins extracellularly to obtain Avipox viruses that can be efficiently recognized by the antigen recognizing cells in host cells. The thus obtained recombinant Avipox viruses are useful as potent vaccines for anti-*Mycoplasma* infection.

---

The invention claimed is:

1. A DNA molecule having a nucleotide sequence coding for a polypeptide having the amino acid sequence set forth in SEQ ID NO: 2.

2. The DNA molecule of claim 1, wherein said DNA has the nucleotide sequence set forth in SEQ ID NO: 1.

3. A DNA molecule having a nucleotide sequence coding for a polypeptide having the amino acid sequence set forth in SEQ ID NO: 4.

4. The DNA molecule of claim 3, wherein said DNA has the nucleotide sequence set forth in SEQ ID NO: 3.

5. A polypeptide having the amino acid sequence set forth in SEQ ID NO: 2.

6. A polypeptide having the amino acid sequence set forth in SEQ ID NO: 4.

* * * * *

SEQUENCE LISTING

```
<160> NUMBER OF SEQ ID NOS:  9

<210> SEQ ID NO 1
<211> LENGTH: 1371
<212> TYPE: DNA
<213> ORGANISM: hybrid

<400> SEQUENCE: 1
atgcactatt ttaggcggaa ttgcatattt ttccttatag ttattctata tggtacgaac      60
tcatctccga gtacccaaaa tgtgacatca agagaagttg tttcgagcgt ccagttgtct     120
gaggaagagt ctacgtttta tctttgtccc ccaccagtgg gttcaaccgt gatccgtcta     180
gaattcggct gtatgtctat tactaaaaaa gatgcaaacc caaataatgg ccaaacccaa     240
ttagaagcag cgcgaatgga gttaacagat ctaatcaatg ctaaagcgat gacattagct     300
tcactacaag actatgccaa gattgaagct agtttatcat ctgcttatag tgaagctgaa     360
acagttaaca ataaccttaa tgcaacatta gaacaactaa aaatggctaa aactaattta     420
gaatcagcca tcaaccaagc taatacggat aaaacgactt ttgataatga acacccaaat     480
```

-continued

```
ttagttgaag catacaaagc actaaaaacc actttagaac aacgtgctac taaccttgaa    540
ggtttgtcat caactgctta taatcaaatt cgcaataatt tagtggatct atacaataaa    600
gctagtagtt taataactaa aacactagat ccactaaatg ggggaacgct tttagattct    660
aatgagatta ctacagctaa taagaatatt aataatacgt tatcaactat taatgaacaa    720
aagactaatg ctgatgcatt atctaatagt tttattaaaa aagtgattca aaataatgaa    780
caaagttttg tagggacttt tacaaacgct aatgttcaac cttcaaacta cagttttgtt    840
gcttttagtg ctgatgtaac acccgtcaat tataaatatg caagaaggac cgtttggaat    900
ggtgatgaac cttcaagtag aattcttgca aacacgaata gtatcacaga tgtttcttgg    960
atttatagtt tagctggaac aaacacgaag taccaattta gttttagcaa ctatggtcca   1020
tcaactggtt atttatattt cccttataag ttggttaaag cagctgatgc taataacgtt   1080
ggattacaat acaaattaaa taatggaaat gttcaacaag ttgagtttgc cacttcaact   1140
agtgcaaata atactacagc taatccaact ccagcagttg atgagattaa agttgctaaa   1200
atcgttttat caggtttaag atttggccaa aacacaatcg aattaagtgt tccaacgggt   1260
gaaggaaata tgaataaagt tgcgccaatg attggcaaca tttatcttag ctcaaatgaa   1320
aataatgctg ataagatccc cgggtaccgt cgacccggta catttttata a            1371
```

<210> SEQ ID NO 2
<211> LENGTH: 456
<212> TYPE: PRT
<213> ORGANISM: hybrid

<400> SEQUENCE: 2

```
Met His Tyr Phe Arg Arg Asn Cys Ile Phe Phe Leu Ile Val Ile Leu
  1               5                  10                  15

Tyr Gly Thr Asn Ser Ser Pro Ser Thr Gln Asn Val Thr Ser Arg Glu
             20                  25                  30

Val Val Ser Ser Val Gln Leu Ser Glu Glu Ser Thr Phe Tyr Leu
         35                  40                  45

Cys Pro Pro Pro Val Gly Ser Thr Val Ile Arg Leu Glu Phe Gly Cys
     50                  55                  60

Met Ser Ile Thr Lys Lys Asp Ala Asn Pro Asn Asn Gly Gln Thr Gln
 65                  70                  75                  80

Leu Glu Ala Ala Arg Met Glu Leu Thr Asp Leu Ile Asn Ala Lys Ala
                 85                  90                  95

Met Thr Leu Ala Ser Leu Gln Asp Tyr Ala Lys Ile Glu Ala Ser Leu
            100                 105                 110

Ser Ser Ala Tyr Ser Glu Ala Glu Thr Val Asn Asn Asn Leu Asn Ala
        115                 120                 125

Thr Leu Glu Gln Leu Lys Met Ala Lys Thr Asn Leu Glu Ser Ala Ile
    130                 135                 140

Asn Gln Ala Asn Thr Asp Lys Thr Thr Phe Asp Asn Glu His Pro Asn
145                 150                 155                 160

Leu Val Glu Ala Tyr Lys Ala Leu Lys Thr Thr Leu Glu Gln Arg Ala
                165                 170                 175

Thr Asn Leu Glu Gly Leu Ser Ser Thr Ala Tyr Asn Gln Ile Arg Asn
            180                 185                 190

Asn Leu Val Asp Leu Tyr Asn Lys Ala Ser Ser Leu Ile Thr Lys Thr
        195                 200                 205

Leu Asp Pro Leu Asn Gly Gly Thr Leu Leu Asp Ser Asn Glu Ile Thr
    210                 215                 220
```

```
Thr Ala Asn Lys Asn Ile Asn Asn Thr Leu Ser Thr Ile Asn Glu Gln
225                 230                 235                 240

Lys Thr Asn Ala Asp Ala Leu Ser Asn Ser Phe Ile Lys Lys Val Ile
            245                 250                 255

Gln Asn Asn Glu Gln Ser Phe Val Gly Thr Phe Thr Asn Ala Asn Val
        260                 265                 270

Gln Pro Ser Asn Tyr Ser Phe Val Ala Phe Ser Ala Asp Val Thr Pro
    275                 280                 285

Val Asn Tyr Lys Tyr Ala Arg Arg Thr Val Trp Asn Gly Asp Glu Pro
290                 295                 300

Ser Ser Arg Ile Leu Ala Asn Thr Asn Ser Ile Thr Asp Val Ser Trp
305                 310                 315                 320

Ile Tyr Ser Leu Ala Gly Thr Asn Thr Lys Tyr Gln Phe Ser Phe Ser
            325                 330                 335

Asn Tyr Gly Pro Ser Thr Gly Tyr Leu Tyr Phe Pro Tyr Lys Leu Val
        340                 345                 350

Lys Ala Ala Asp Ala Asn Asn Val Gly Leu Gln Tyr Lys Leu Asn Asn
    355                 360                 365

Gly Asn Val Gln Gln Val Glu Phe Ala Thr Ser Thr Ser Ala Asn Asn
370                 375                 380

Thr Thr Ala Asn Pro Thr Pro Ala Val Asp Glu Ile Lys Val Ala Lys
385                 390                 395                 400

Ile Val Leu Ser Gly Leu Arg Phe Gly Gln Asn Thr Ile Glu Leu Ser
            405                 410                 415

Val Pro Thr Gly Glu Gly Asn Met Asn Lys Val Ala Pro Met Ile Gly
        420                 425                 430

Asn Ile Tyr Leu Ser Ser Asn Glu Asn Asn Ala Asp Lys Ile Pro Gly
    435                 440                 445

Tyr Arg Arg Pro Gly Thr Phe Leu
    450                 455

<210> SEQ ID NO 3
<211> LENGTH: 3261
<212> TYPE: DNA
<213> ORGANISM: hybrid

<400> SEQUENCE: 3
atgcactatt ttaggcggaa ttgcatattt ttccttatag ttattctata tggtacgaac     60
tcatctccga gtacccaaaa tgtgacatca agagaagttg tttcgagcgt ccagttgtct    120
gaggaagagt ctacgtttta tctttgtccc ccaccagtgg gttcaaccgt gatccgtcta    180
gaaccgccgc gaaatgtccc gaacctaga aaagccaccg agtggggtga aggaatcgcg     240
atattattta aagagaatat cagtccatat aaatttaaag tgacgcttta ttataaaaat    300
atcattcaga cgacgacatg gacggggacg acatatagac agatcactaa tcgatataca    360
gataggacgc ccgtttccat tgaagagatc acggatctaa tcgacggcaa aggaagatgc    420
tcatctaaag caagatacct tagaaacaat gtatatgttg aagcgtttga cagggatgcg    480
ggagaaaaac aagtacttct aaaaccatca aaattcaaca cgcccgaatc tagggcatgg    540
cacacgacta atgagacgta taccgtgtgg ggatcaccat ggatatatcg aacgggaacc    600
tccgtcaatt gtatagtaga ggaaatggat gcccgctctg tgtttccgta ttcatatttt    660
gcaatggcca atgcgacat cgcgaacata tctccatttt atggtctatc cccaccagag     720
gctgccgcag aacccatggg atatccccag gataatttca acaactaga tagctatttt    780
```

```
tcaatggatt tggacaagcg tcgaaaagca agccttccag tcaagcgtaa ctttctcatc    840
acatcacact tcacagttgg gtgggactgg gctccaaaaa ctactcgtgt atgttcaatg    900
actaagtgga aagaggtgac tgaaatgttg cgtgcaacag ttaatgggag atacagattt    960
atggcccgtg aactttcggc aacgtttatc agtaatacga ctgagtttga tccaaatcgc   1020
atcatattag acaatgtat  taaacgcgag gcagaagcag caatcgagca gatatttagg   1080
acaaaatata atgacagtca cgtcaaggtt ggacatgtac aatatttctt ggctctcggg   1140
ggatttattg tagcatatca gcctgttcta tccaaatccc tggctcatat gtacctcaga   1200
gaattgatga gagacaacag gaccgatgag atgctcgacc tggtaaacaa taagcatgca   1260
atttataaga aaaatgctac ctcattgtca cgattgcggc gagatattcg aaatgcacca   1320
aatagaaaaa taacattaga cgacaccaca gctattaaat cgacatcgtc tgttcaattc   1380
gccatgctcc aatttcttta tgatcatata caaacccata ttaatgatat gtttagtagg   1440
attgccacag cttggtgcga attgcagaat agagaacttg ttttatggca cgaagggata   1500
aagattaatc ctagcgctac agcgagtgca acattaggaa ggagagtggc tgcaaagatg   1560
ttgggggatg tcgctgctgt atcgagctgc actgctatag atgcggaatc cgtcactttg   1620
caaaattcta tgcgagttat cacatccact aatacatgtt atagccgacc attggttcta   1680
ttttcatatg gagaaaacca aggaaacata cagggacaac tcggtgaaaa caacgagttg   1740
cttccaacgc tagaggctgt agagccatgc tcggctaatc atcgtagata ttttctgttt   1800
ggatccggtt atgctttatt tgaaaactat aattttgtta agatggtaga cgctgccgat   1860
atacagattg ctagcacatt tgtcgagctt aatctaaccc tgctagaaga tcgggaaatt   1920 ttgccttat  ccgtttacac aaaagaagag ttgcgtgatg ttggtgtatt ggattatgca   1980
gaagtagctc gccgcaatca actacatgaa cttaaatttt atgacataaa caaagtaata   2040
gaagtggata caaattacgc ggggctgcag gaattcggct gtatgtctat tactaaaaaa   2100
gatgcaaacc caaataatgg ccaaacccaa ttagaagcag cgcgaatgga gttaacagat   2160
ctaatcaatg ctaaagcgat gacattagct tcactacaag actatgccaa gattgaagct   2220
agtttatcat ctgcttatag tgaagctgaa acagttaaca ataaccttaa tgcaacatta   2280
gaacaactaa aaatggctaa aactaattta gaatcagcca tcaaccaagc taatacggat   2340
aaaacgactt ttgataatga acacccaaat ttagttgaag catacaaagc actaaaaacc   2400
actttagaac aacgtgctac taaccttgaa ggtttgtcat caactgctta taatcaaatt   2460
cgcaataatt tagtggatct atacaataaa gctagtagtt taataactaa acactagat   2520 ccactaaatg ggggaacgct tttagattct aatgagatta ctacagctaa taagaatatt   2580
aataatacgt tatcaactat taatgaacaa aagactaatg ctgatgcatt atctaatagt   2640
tttattaaaa aagtgattca aaataatgaa caaagtttg tagggacttt tacaaacgct   2700
aatgttcaac cttcaaacta cagttttgtt gcttttagtg ctgatgtaac acccgtcaat   2760
tataaatatg caagaaggac cgtttggaat ggtgatgaac cttcaagtag aattcttgca   2820
aacacgaata gtatcacaga tgtttcttgg atttatagtt tagctggaac aaaacgaag   2880 taccaattta gttttagcaa ctatggtcca tcaactggtt attttatttt cccttataag   2940
ttggttaaag cagctgatgc taataacgtt ggattacaat acaaattaaa taatggaaat   3000
gttcaacaag ttgagtttgc cacttcaact agtgcaaata atactacagc taatccaact   3060
ccagcagttg atgagattaa agttgctaaa atcgtttat  caggtttaag atttggccaa   3120
```

-continued

```
aacacaatcg aattaagtgt tccaacgggt gaaggaaata tgaataaagt tgcgccaatg    3180
attggcaaca tttatcttag ctcaaatgaa aataatgctg ataagatccc cgggtaccgt    3240
cgacccggta cattttttata a                                             3261
```

<210> SEQ ID NO 4
<211> LENGTH: 1086
<212> TYPE: PRT
<213> ORGANISM: hybrid

<400> SEQUENCE: 4

```
Met His Tyr Phe Arg Arg Asn Cys Ile Phe Phe Leu Ile Val Ile Leu
  1               5                  10                  15

Tyr Gly Thr Asn Ser Ser Pro Ser Thr Gln Asn Val Thr Ser Arg Glu
             20                  25                  30

Val Val Ser Ser Val Gln Leu Ser Glu Glu Ser Thr Phe Tyr Leu
         35                  40                  45

Cys Pro Pro Val Gly Ser Thr Val Ile Arg Leu Glu Pro Pro Arg
     50                  55                  60

Lys Cys Pro Glu Pro Arg Lys Ala Thr Glu Trp Gly Glu Gly Ile Ala
 65                  70                  75                  80

Ile Leu Phe Lys Glu Asn Ile Ser Pro Tyr Lys Phe Lys Val Thr Leu
                 85                  90                  95

Tyr Tyr Lys Asn Ile Ile Gln Thr Thr Thr Trp Thr Gly Thr Thr Tyr
            100                 105                 110

Arg Gln Ile Thr Asn Arg Tyr Thr Asp Arg Thr Pro Val Ser Ile Glu
        115                 120                 125

Glu Ile Thr Asp Leu Ile Asp Gly Lys Gly Arg Cys Ser Ser Lys Ala
    130                 135                 140

Arg Tyr Leu Arg Asn Asn Val Tyr Val Glu Ala Phe Asp Arg Asp Ala
145                 150                 155                 160

Gly Glu Lys Gln Val Leu Leu Lys Pro Ser Lys Phe Asn Thr Pro Glu
                165                 170                 175

Ser Arg Ala Trp His Thr Thr Asn Glu Thr Tyr Thr Val Trp Gly Ser
            180                 185                 190

Pro Trp Ile Tyr Arg Thr Gly Thr Ser Val Asn Cys Ile Val Glu Glu
        195                 200                 205

Met Asp Ala Arg Ser Val Phe Pro Tyr Ser Tyr Phe Ala Met Ala Asn
    210                 215                 220

Gly Asp Ile Ala Asn Ile Ser Pro Phe Tyr Gly Leu Ser Pro Pro Glu
225                 230                 235                 240

Ala Ala Ala Glu Pro Met Gly Tyr Pro Gln Asp Asn Phe Lys Gln Leu
                245                 250                 255

Asp Ser Tyr Phe Ser Met Asp Leu Asp Lys Arg Arg Lys Ala Ser Leu
            260                 265                 270

Pro Val Lys Arg Asn Phe Leu Ile Thr Ser His Phe Thr Val Gly Trp
        275                 280                 285

Asp Trp Ala Pro Lys Thr Thr Arg Val Cys Ser Met Thr Lys Trp Lys
    290                 295                 300

Glu Val Thr Glu Met Leu Arg Ala Thr Val Asn Gly Arg Tyr Arg Phe
305                 310                 315                 320

Met Ala Arg Glu Leu Ser Ala Thr Phe Ile Ser Asn Thr Thr Glu Phe
                325                 330                 335

Asp Pro Asn Arg Ile Ile Leu Gly Gln Cys Ile Lys Arg Glu Ala Glu
            340                 345                 350
```

```
Ala Ala Ile Glu Gln Ile Phe Arg Thr Lys Tyr Asn Asp Ser His Val
        355                 360                 365
Lys Val Gly His Val Gln Tyr Phe Leu Ala Leu Gly Gly Phe Ile Val
        370                 375                 380
Ala Tyr Gln Pro Val Leu Ser Lys Ser Leu Ala His Met Tyr Leu Arg
385                 390                 395                 400
Glu Leu Met Arg Asp Asn Arg Thr Asp Glu Met Leu Asp Leu Val Asn
                405                 410                 415
Asn Lys His Ala Ile Tyr Lys Lys Asn Ala Thr Ser Leu Ser Arg Leu
            420                 425                 430
Arg Arg Asp Ile Arg Asn Ala Pro Asn Arg Lys Ile Thr Leu Asp Asp
            435                 440                 445
Thr Thr Ala Ile Lys Ser Thr Ser Ser Val Gln Phe Ala Met Leu Gln
        450                 455                 460
Phe Leu Tyr Asp His Ile Gln Thr His Ile Asn Asp Met Phe Ser Arg
465                 470                 475                 480
Ile Ala Thr Ala Trp Cys Glu Leu Gln Asn Arg Glu Leu Val Leu Trp
                485                 490                 495
His Glu Gly Ile Lys Ile Asn Pro Ser Ala Thr Ala Ser Ala Thr Leu
            500                 505                 510
Gly Arg Arg Val Ala Ala Lys Met Leu Gly Asp Val Ala Ala Val Ser
        515                 520                 525
Ser Cys Thr Ala Ile Asp Ala Glu Ser Val Thr Leu Gln Asn Ser Met
        530                 535                 540
Arg Val Ile Thr Ser Thr Asn Thr Cys Tyr Ser Arg Pro Leu Val Leu
545                 550                 555                 560
Phe Ser Tyr Gly Glu Asn Gln Gly Asn Ile Gln Gly Gln Leu Gly Glu
                565                 570                 575
Asn Asn Glu Leu Leu Pro Thr Leu Glu Ala Val Glu Pro Cys Ser Ala
            580                 585                 590
Asn His Arg Arg Tyr Phe Leu Phe Gly Ser Gly Tyr Ala Leu Phe Glu
        595                 600                 605
Asn Tyr Asn Phe Val Lys Met Val Asp Ala Ala Asp Ile Gln Ile Ala
        610                 615                 620
Ser Thr Phe Val Glu Leu Asn Leu Thr Leu Leu Glu Asp Arg Glu Ile
625                 630                 635                 640
Leu Pro Leu Ser Val Tyr Thr Lys Glu Glu Leu Arg Asp Val Gly Val
                645                 650                 655
Leu Asp Tyr Ala Glu Val Ala Arg Arg Asn Gln Leu His Glu Leu Lys
            660                 665                 670
Phe Tyr Asp Ile Asn Lys Val Ile Glu Val Asp Thr Asn Tyr Ala Gly
        675                 680                 685
Leu Gln Glu Phe Gly Cys Met Ser Ile Thr Lys Lys Asp Ala Asn Pro
        690                 695                 700
Asn Asn Gly Gln Thr Gln Leu Glu Ala Ala Arg Met Glu Leu Thr Asp
705                 710                 715                 720
Leu Ile Asn Ala Lys Ala Met Thr Leu Ala Ser Leu Gln Asp Tyr Ala
                725                 730                 735
Lys Ile Glu Ala Ser Leu Ser Ser Ala Tyr Ser Glu Ala Glu Thr Val
            740                 745                 750
Asn Asn Asn Leu Asn Ala Thr Leu Glu Gln Leu Lys Met Ala Lys Thr
        755                 760                 765
```

-continued

Asn Leu Glu Ser Ala Ile Asn Gln Ala Asn Thr Asp Lys Thr Thr Phe
    770             775                 780

Asp Asn Glu His Pro Asn Leu Val Glu Ala Tyr Lys Ala Leu Lys Thr
785             790                 795                 800

Thr Leu Glu Gln Arg Ala Thr Asn Leu Glu Gly Leu Ser Ser Thr Ala
            805                 810                 815

Tyr Asn Gln Ile Arg Asn Asn Leu Val Asp Leu Tyr Asn Lys Ala Ser
        820                 825                 830

Ser Leu Ile Thr Lys Thr Leu Asp Pro Leu Asn Gly Gly Thr Leu Leu
    835                 840                 845

Asp Ser Asn Glu Ile Thr Thr Ala Asn Lys Asn Ile Asn Asn Thr Leu
850                 855                 860

Ser Thr Ile Asn Glu Gln Lys Thr Asn Ala Asp Ala Leu Ser Asn Ser
865                 870                 875                 880

Phe Ile Lys Lys Val Ile Gln Asn Asn Glu Gln Ser Phe Val Gly Thr
            885                 890                 895

Phe Thr Asn Ala Asn Val Gln Pro Ser Asn Tyr Ser Phe Val Ala Phe
        900                 905                 910

Ser Ala Asp Val Thr Pro Val Asn Tyr Lys Tyr Ala Arg Arg Thr Val
    915                 920                 925

Trp Asn Gly Asp Glu Pro Ser Ser Arg Ile Leu Ala Asn Thr Asn Ser
930                 935                 940

Ile Thr Asp Val Ser Trp Ile Tyr Ser Leu Ala Gly Thr Asn Thr Lys
945                 950                 955                 960

Tyr Gln Phe Ser Phe Ser Asn Tyr Gly Pro Ser Thr Gly Tyr Leu Tyr
            965                 970                 975

Phe Pro Tyr Lys Leu Val Lys Ala Ala Asp Ala Asn Asn Val Gly Leu
        980                 985                 990

Gln Tyr Lys Leu Asn Asn Gly Asn Val Gln Gln Val Glu Phe Ala Thr
    995                 1000                1005

Ser Thr Ser Ala Asn Asn Thr Thr Ala Asn Pro Thr Pro Ala Val Asp
   1010                 1015                1020

Glu Ile Lys Val Ala Lys Ile Val Leu Ser Gly Leu Arg Phe Gly Gln
1025                1030                1035                1040

Asn Thr Ile Glu Leu Ser Val Pro Thr Gly Glu Gly Asn Met Asn Lys
                1045                1050                1055

Val Ala Pro Met Ile Gly Asn Ile Tyr Leu Ser Ser Asn Glu Asn Asn
            1060                1065                1070

Ala Asp Lys Ile Pro Gly Tyr Arg Arg Pro Gly Thr Phe Leu
        1075                1080                1085

<210> SEQ ID NO 5
<211> LENGTH: 86
<212> TYPE: DNA
<213> ORGANISM: Artificial Sequence
<220> FEATURE:
<223> OTHER INFORMATION: Description of Artificial Sequence:
      modification of Davidson's promoter

<400> SEQUENCE: 5
tttttttttt ttggcatata aataataata aatacaataa ttaattacgc gtaaaaattg    60
aaaaactatt ctaatttatt gcactc                                         86

<210> SEQ ID NO 6
<211> LENGTH: 91
<212> TYPE: DNA

```
<213> ORGANISM: Artificial Sequence
<220> FEATURE:
<223> OTHER INFORMATION: Description of Artificial Sequence:
      modification of Davidson's promoter

<400> SEQUENCE: 6 ttttttttt  ttttttttt  ggcatataaa  taataaatac  aataattaat  tacgcgtaaa        60
aattgaaaaa  ctattctaat  ttattgcact  c                                      91

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: insertion
      at HindIII-PstI site of modified pUC18

<400> SEQUENCE: 7
agctgccccc  ccggcaagct  tgca                                               24

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: insertion
      at SalI-EcoRI site of modified pUC18

<400> SEQUENCE: 8
tcgacatttt  tatgtgtac                                                      19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: insertion
      at SacI-EcoRI site of modified pUC18

<400> SEQUENCE: 9
aatcggccgg  gggggccagc  t                                                  21
```